United States Patent [19]

Albarella

[11] Patent Number: 4,469,797
[45] Date of Patent: Sep. 4, 1984

[54] DIGOXIGENIN IMMUNOGENS, ANTIBODIES, LABELED CONJUGATES, AND RELATED DERIVATIVES

[75] Inventor: James P. Albarella, Elkhart, Ind.

[73] Assignee: Miles Laboratories, Inc., Elkhart, Ind.

[21] Appl. No.: 422,217

[22] Filed: Sep. 23, 1982

[51] Int. Cl.$^3$ .................... G01N 33/54; G01N 33/58
[52] U.S. Cl. ............................. 436/536; 260/239.57; 260/112 B; 436/537; 436/544; 436/546; 436/800; 436/817; 435/4; 435/7; 435/28
[58] Field of Search ...................... 260/239.57, 112 B; 436/536, 537, 544, 546, 800, 817; 435/28, 4, 7

[56] References Cited

U.S. PATENT DOCUMENTS

| | | | |
|---|---|---|---|
| 3,855,208 | 12/1974 | Rutner et al. | 260/239.57 |
| 3,953,431 | 4/1976 | Kutner et al. | 260/239.57 |
| 4,082,747 | 4/1978 | Chen | 260/239.57 |

FOREIGN PATENT DOCUMENTS

| | | | |
|---|---|---|---|
| 2621507 | 12/1976 | Fed. Rep. of Germany | 260/239.57 |
| 1441101 | 6/1976 | United Kingdom | 260/239.57 |
| 2003480 | 3/1979 | United Kingdom | 260/239.57 |
| 1544159 | 4/1979 | United Kingdom | 260/239.57 |

OTHER PUBLICATIONS

Hauser et al., Chem. Abstracts, vol. 80, (1974), No. 60080n.

*Primary Examiner*—Christine M. Nucker
*Attorney, Agent, or Firm*—Andrew L. Klawitter

[57] ABSTRACT

Immunogen conjugates comprising N-substituted-amino-3-desoxydigoxigenin derivatives coupled to conventional immunogenic carrier materials, and antibodies raised against such conjugates. Also provided are labeled digoxigenin conjugates for use with the digoxigenin antibodies in preferred immunoassay techniques for determining digoxin in biological fluids.

22 Claims, No Drawings

DIGOXIGENIN IMMUNOGENS, ANTIBODIES, LABELED CONJUGATES, AND RELATED DERIVATIVES

BACKGROUND OF THE INVENTION

1. Field of the Invention

This invention relates to immunogen conjugates comprising digoxigenin derivatives, particularly carboxy- and amino-functionalized derivatives coupled to conventional immunogenic carrier materials, and anti-digoxin antibodies prepared against such immunogen conjugates. Such antibodies are useful in immunoassays for determining digoxin in biological fluids. The invention also relates to labeled digoxigenin conjugates useful in particularly preferred immunoassay techniques.

2. Background of the Invention

It is of established medical value to monitor the concentration of digoxin in the bloodstream of patients under treatment with the drug. Immunoassays are the currently most common methods used to determine digoxin in blood samples, e.g., serum or plasma, and are based on the specific binding of anti-digoxin antibodies to the drug in the test sample.

Digoxin is a cardiac glycoside consisting of an aglycone, digoxigenin, and three glycosidic digitoxose residues linked to the aglycone at the C-3 position. The glycoside is a hapten, that is, it is incapable of stimulating antibody production unless it is injected into the host animal in the form of a conjugate with an immunogenic carrier material, e.g., a protein such as albumin from an animal of a different species. The conventional immunogen conjugate for preparing anti-digoxin antibodies comprises the glycoside chemically linked through a modification of the terminal glycosidic residue to a carrier. The terminal residue is oxidized with periodate to open the ring and form a dialdehyde derivative which is readily couplable to free amino groups in the carrier [Butler and Chen, *Proc. Natl. Acad. Sci. USA* 57:71(1967), and Smith et al, *Biochem* 9:331(1970)]. The result is a digoxin-carrier conjugate.

Antibodies against the related cardiac glycoside digitoxin have been prepared from a conjugate of the aglycone coupled at the C-3 position to the carrier. The aglycone 3-o-succinoyl-digitoxigenin has been coupled by conventional techniques to protein carriers [Oliver et al, *J. Clin. Invest.* 47:1035(1968)].

3-Substituted digoxigenin and digitoxigenin derivatives have been proposed and used for the purpose of preparing labeled conjugates to be used in conjunction with anti-digoxin and anti-digitoxin antibodies in performing immunoassays. Representative of this art are U.S. Pat. Nos. 3,981,982 and 4,064,227 and U.S. Pat. Nos. 4,039,385; 4,213,893; and 4,273,866 relating to various nonradioisotopically labeled conjugates.

U.S. Pat. Nos. 4,217,280 and 4,219,549 describe the synthesis of various 3-amino-3-desoxydigoxigenin derivatives and their use in cardiotonic therapy. The preparation of 3-digoxigenone is known from Tamm and Gubler, *Helv. Chim. Acta* 42:239(1959) and Shimizu and Mituhashi, *Tetrahedron* 24:4207(1968). Boutique and Koenig, *Bull. Chem. Soc. Fr.* 1973(2), part 2, 750 describe the reductive amination of steroidal ketones. The use of sodium cyanoborohydride in the reductive amination of aldehydes and ketones is described by Borch et al, *J. Amer. Chem. Soc.* 93:2987(1971). 3-Aminocardenolides were prepared by Hanser et al, *Helv. Chim. Acta* 56(8):2782(1973).

SUMMARY OF THE INVENTION

The present invention provides digoxigenin immunogen conjugates comprising 3-[N-(carboxyalkyl)]-amino-3-desoxydigoxigenin or 3-[N-(aminoalkyl)]-amino-3-desoxydigoxigenin derivatives coupled to conventional immunogenic carrier materials. The immunogens provided are of the general formula:

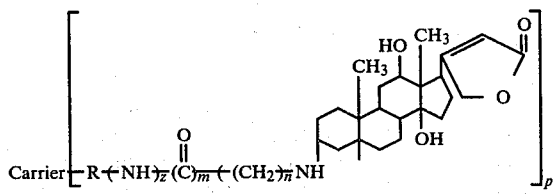

wherein Carrier is the carrier material, R is a bond or a linking group, one of l and m is one and the other is zero, n is an integer from 2 through 10, and p is on the average from 1 to about 50. When linking group R is a bond, the digoxigenin derivative is coupled directly to the carrier material, for example by amide linkages between the amino or carboxyl group of the derivative and carboxyl or amino groups, respectively, on the carrier, which in such case is usually a protein or a polypeptide. When bridge group R is other than a simple bond, it may comprise a wide variety of conventional structures, for example, the residue of a bifunctional coupling agent linking the amino or carboxyl terminal group of the digoxigenin moiety to appropriate groups on the carrier, usually amino or carboxyl groups.

Also provided are anti-digoxin antibodies prepared against such conjugates according to conventional antiserum or monoclonal techniques. Such antibodies are useful in immunoassay methods and reagent means, such as test kits and test devices, for determining digoxin.

Labeled conjugates useful in particularly preferred homogeneous, nonradioisotopic immunoassay techniques are also provided, as well as novel digoxigenin derivatives used in the synthesis of such labeled conjugates and the immunogen conjugates.

DESCRIPTION OF THE PREFERRED EMBODIMENTS

The N-functionalized-amino-3-desoxydigoxigenin derivatives are the carboxyalkyl and aminoalkyl derivatives of the formula:

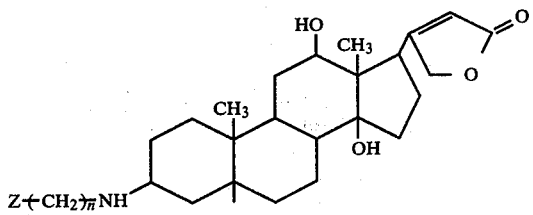

wherein Z is amino or carboxyl and n is an integer from 2 through 10. Such derivatives are prepared by reductive amination of 3-digoxigenone with the appropriate, α,ω-alkanediamine or ω-aminoalkanoic acid in the presence of sodium cyanoborohydride.

In a preferred embodiment, the functionalized digoxigenin derivatives are coupled directly to corresponding amino or carboxyl groups in the carrier material by formation of an amide or peptide couple. The resulting preferred immunogen conjugates have the formula:

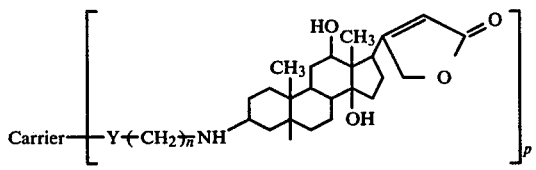

wherein Carrier and n are as defined above, Y is an amide group linking carboxyl or amino groups on the carrier material, which usually is an immunogenic protein or polypeptide, to the digoxigenin moiety, and p is on the average from 1 to the number of available amide coupling sites (e.g., available carboxyl or amino groups, as the case may be, under the coupling conditions) on the carrier, usually less than about 50.

The peptide condensation reactions available for performing the direct coupling of the digoxigenin derivative to a carboxyl group-containing carrier are well known and include, without limitation, the carbodiimide reaction [Aherne et al, *Brit. J. Clin. Pharm.* 3:56(1976) and *Science* 144:1344(1974)], the mixed anhydride reaction [Erlanger et al, *Methods in Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also *Clin. Chem.* 22:726(1976).

Alternatively, the digoxigenin derivatives can be coupled through the use of a conventional linking reagent that forms a bond at one end with the amino or carboxyl group in the derivative and a bond at the other end with an appropriate functional group present on the carrier. For example, bifunctional coupling reagents are well known for coupling amine derivatives to amine macromolecules, including bis-imidates, bis-isocyanates, and glutaraldehyde [*Immuno-chem.* 6:53(1959)]. Other useful coupling reactions are thoroughly discussed in the literature, for instance in the above-mentioned Kopple monograph; Lowe and Dean, *Affinity Chromatography*, John Wiley and Sons (New York 1974); Means and Feeney, *Chemical Modification of Proteins*, Holden-Day (San Francisco 1971); and Glazer et al, *Chemical Modification of Proteins*, Elsevier (New York 1975).

The quantity p in the above formulas represents the number of digoxigenin moieties that are conjugated to the carrier, i.e., the epitopic density of the immunogen, and in the unusual situation will be on the average from 1 to about 50, more normally from 1 to about 20. Optimal epitopic densities, considering the ease and reproducibility of synthesis of the immunogen and antibody response, fall between about 2 and about 15, more usually between 4 and 10.

The immunogenic carrier material can be selected from any of those conventionally known having available functional groups for coupling to the digoxigenin derivatives. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., a glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, N.J. USA, 1976); Butler, *J. Immunol. Meth.* 7:1-24(1974); Weinryb and Schroff, *Drug Metab Rev.* 10:271-283(1975); Broughton and Strong, *Clin. Chem.* 22:726-732(1976); and Playfair et al, *Br. Med. Bull.* 30:24-31(1974).

Preparation of specific antibodies using the present immunogen conjugates may follow any conventional technique. Numerous texts are available describing the fundamental aspects of inducing antibody formation; for example reference may be made to Parker, *Radioimmunoassay of Biologically Active Compounds*, Prentice-Hall (Englewood Cliffs, N.J. USA, 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that an acceptable titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266:495(1977), and *Science* 208:692 (1980).

The antibodies prepared from the immunogens of the present invention can be used in any immunoassay method, and the corresponding reagent means, for determining digoxin, including agglutination techniques, radioimmunoassays, heterogeneous enzyme immunoassays (see U.S. Pat. No. 3,654,090), heterogeneous fluorescent immunoassays (see U.S. Pat. Nos. 4,201,763; 4,133,639 and 3,992,631), and homogeneous (separation-free) immunoassays. The latter-most are particularly preferred and include such techniques as fluorescence quenching or enhancement (see U.S. Pat. No. 4,160,016), fluorescence polarization (see *J. Exp. Med.* 122:1029(1965), enzyme substrate-labeled immunoassay (see U.S. Pat. No. 4,279,992 and U.K. Pat. No. 1,552,607), prosthetic group-labeled immunoassay (see U.S. Pat. No. 4,238,565), enzyme modulator-labeled immunoassay, e.g., using inhibitor labels (see U.S. Pat. Nos. 4,134,972 and 4,273,866), enzyme-labeled immunoassay (see U.S. Pat. No. 3,817,837), energy transfer immunoassay (see U.S. Pat. No. 3,996,345), chemically-excited fluorescence immunoassay (see U.S. Pat. No. 4,238,195) and double antibody steric hindrance immunoassay (see U.S. Pat. Nos. 3,935,074 and 3,998,943).

Moreover, the derivatives of the present invention can be used to prepare the labeled conjugates needed to perform the various immunoassays described above. Appropriate derivatives can be radio-labeled or labeled with fluorescent moieties in accordance with standard methods. Likewise the appropriate labeling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the derivatives to yield labeled conjugates.

One type of preferred labeled conjugate is that labeled with β-galactosyl-umbelliferone (βGU), having the general formula:

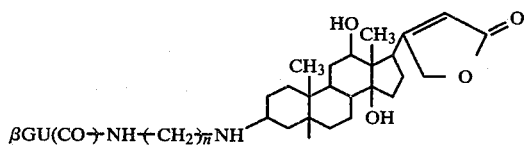

wherein βGU(CO→ is

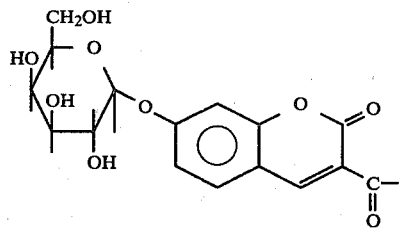

and n is as defined above. Preferably, such conjugates are prepared by conventional peptide condensations of βGU-carboxylic acid (U.S. Pat. No. 4,226,978) with the appropriate 3-[N-(aminoalkyl)]-amino-3-desoxydigoxigenin derivative. The βBGU-labeled conjugates are useful as labeled reagents in substrate-labeled fluorescent immunoassays (SLFIA-see U.S. Pat. No. 4,279,992).

Another type of labeled conjugate is that labeled with flavin adenine dinucleotide (FAD), having the general formula:

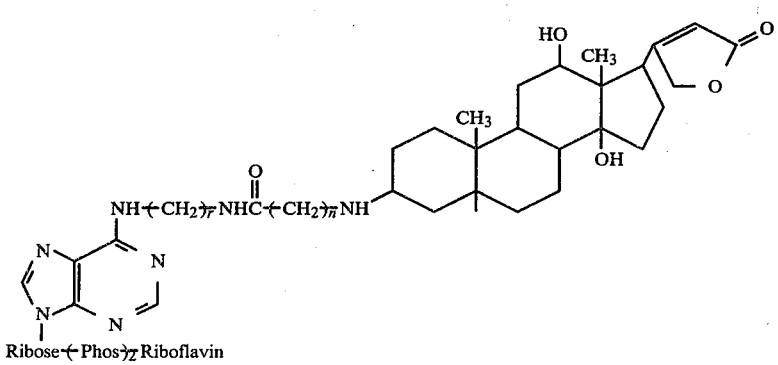

wherein Ribose—(Phos)₂ Riboflavin represents the riboflavin-pyrophosphate-ribose residue in FAD, r is an integer from 2 through 10, and n is as defined above. Such conjugates are prepared by peptide condensation of an appropriate $N^6$-ω-aminoalkyl-FAD derivative (U.S. Pat. No. 4,255,566) with the appropriate N-(carboxyalkyl)-amino-3-desoxydigoxigenin derivative. The FAD-labeled conjugates are useful as labeled reagents in apoenzyme reactivation immunoassay systems (ARIS-see U.S. Pat. No. 4,238,565).

The reagent means of the present invention comprises all of the essential chemical elements required to conduct a desired digoxin immunoassay method encompassed by the present invention. The reagent means or system is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired, e.g., an antibody and labeled conjugate of the present invention. Of course, the reagent means can include other materials as are known in the art and which may be desirable from a commercial and user standpoint, such as buffers, diluents, standards, and so forth. Particularly preferred is a test kit for the homogeneous competitive binding immunoassay of the present invention comprising (a) an anti-digoxin antibody of the present invention and (b) a labeled digoxigenin conjugate which has a detectable property which is altered when bound with the antibody. Also preferred is a test device comprising the reagent composition and a solid carrier member incorporated therewith. The various forms of such test device are described in U.S. patent application Ser. No. 202,378, filed Oct. 30, 1980, which is incorporated herein by reference and which has published as European patent application No. 51,213. The specific label used in the preferred test kit and test device will depend on the technique followed, as described hereinabove.

The present invention will now be illustrated, but is not intended to be limited, by the following examples.

EXAMPLE 1

Preparation of digoxigenin derivatives

3-N-(6-Aminohexyl)amino-3-desoxydigoxigenin

A mixture of 1 gram (g) 3-digoxigenone [Tamm and Gubler, *Helv. Chim. Acta*, 42:239(1959) and Shimizu and Mituhashi, *Tetrahedron* 24:4207(1968)] (2.58 mmol), 3.21 g 1,6-hexanediamine (27.6 mmol), and 50 milliliters (ml) methanol (CH₃OH) was adjusted to pH 6 with glacial acetic acid and treated with 125 milligrams (mg)

sodium cyanoborohydride (1.99 mmol). After stirring overnight, the mixture was preadsorbed onto 5 g silica gel (SiO₂) and chromatographed over 200 g SiO₂-60 (E. Merck, West Germany) eluted first with 3 liters (L) of the lower phase of a 2:1:1 chloroform ($CHCl_3$)—$CH_3OH$-14% ammonium hydroxide ($NH_4OH$) mixture followed by 3 L of the lowr phase of a 2:1:1 $CHCl_3$—$CH_3OH$-28% $NH_4OH$ mixture. A partial separation of one of the two 3α and β-isomers of the product was achieved. The fractions containing this product were pooled, concentrated, and precipitated as an amorphous white powder from isopropanol-1:1 (ether-hexane). Yield 336 mg (27%).

Analysis: Calculated for $C_{29}H_{28}N_2O_4 \cdot \frac{1}{2}H_2O$: C, 69,98; H, 10.06; N, 5.63. Found: C, 69.68; H, 9.61; N, 5.71.

¹H NMR (90 mHz, DMSO-d₆): δ0.66 (s,3H); 0.85 (s,3H); 1.29 (m,28H); 2.35 (m,3H); 7.11 (m,7H); 4.09 (m,1H); 4.87 (s,2H); 5.81 (s,1H).

IR (KCl): 2940, 2870, 1740, 1625, 1395, 1025 cm⁻¹.

3-N-(5-Carboxypentyl)amino-3-desoxydigoxigenin

To a suspension of 300 mg 3-digoxigenone (0.77 mmol) and 506 mg 6-aminocarproic acid (3.86 mmol) in 30 mL $CH_3OH$ was added 253 mg sodium cyanoborohydride. The mixture was allowed to stir overnight at room temperature. The reaction mixture was quenched with 0.5 Ml $H_2O$ and evaporated under reduced pressure. The residue was taken up in 10 ml $CH_3OH$, preadsorbed on 1 g $SiO_2$, and chromatographed over a 3.5×18 cm column of $SiO_2$ eluted with the lower phase of a 1:1:1: $CHCl_3CH_3OH$-conc.$NH_4OH$ mixture. The fractions containing the desired product were pooled and evaporated to give 596 mg of a colorless glass. The sample was dissolved in 2 ml $H_2O$ and chromatographed over a 2.5×90 cm column of Sephadex® LH-20 (Pharmacia, Piscataway, NJ, USA) eluted with $H_2O$. The fractions containing the product as a mixture of C-3 isomers were pooled and evaporated. The product was obtained as a white powder from $CH_3OH$/ether-petroleum ether. Yield 279 mg (72%). mp 172°–180° C.

Analysis: Calculated for $C_{29}H_{45}NO_6 \cdot \frac{1}{2}H_2O$: C, 68.01; H, 9.04; N, 2.73. Found: C, 68.14; H, 9.26; N, 2.47.

¹H NMR (90 mHz, DMSO-d₆): δ0.65 (s,3H; 0.85 (s,3H); 1.38 (m,31H); 2.5 (m,2H); 2.97 (m,1H); 3.23 (m,2H); 4.02 ($H_2O$); 4.87 (s,2H); 5.82 (s,1H).

(IR (KCl): 2940, 2860, 1780, 1745, 1625, 1570, 1455, 1400 cm⁻¹.

EXAMPLE 2

Preparation of anti-digoxin antibodies

Thirteen milligrams of 3-N-(5-carboxypentyl) amino-3-desoxydigoxigenin was dissolved in 0.3 ml of dry dimethylformamide containing 7 μl of tri-n-butylamine, and this mixture was cooled in an ice bath. Ten microliters (μl) of ethyl chloroformate was added and allowed to react for 15 minutes. This reaction mixture was added dropwise to a stirred solution of 125 mg bovine serum albumin in 5 ml water containing 125 μl 1.0N sodium hydroxide (NaOH). Twenty-four hours later the reaction was chromatographed on a 2.5×55 cm column of Sephadex® G-25 (coarse) (Pharmacia) equilibrated with 0.1M sodium phosphate buffer, pH 7.0, and 10.5 ml fractions were collected. The absorbance at 280 nanometers (nm) of fraction 13 was recorded. Also, 200 μl of this fraction was mixed with 0.8 ml of concentrated sulfuric acid and the optical absorption spectrum was recorded from 340 to 450 nm. The absorbance at 380 nm taken from this spectrum was used to calculate the amount of digoxigenin derivative coupled to bovine serum albumin assuming that the millimolar extinction coefficient at 380 nm for the digoxigenin derivative is 3.2. The hapten:protein molar ratio was 8.6.

Fractions 12 to 15 from the chromatography were pooled and used for immunization. This pool was diluted with 0.1M sodium phosphate buffer, pH 7.0, to give a protein concentration of 0.4 mg/ml. One milliliter of this immunogen was combined with 1 ml of complete Freund's adjuvant and injected subcutaneously into a rabbit. A booster immunization was administered at four week intervals and for these the immunogen was combined with incomplete Freund's adjuvant. Test bleedings were taken one week after the boosters. Five months after the initial immunization, antiserum with suitable titer was obtained.

EXAMPLE 3

Preparation of labeled digoxigenin conjugates

3-N-6-(7-β-galactosylcoumarin-3-carboxamidohexyl-)amino-3-desoxydigoxigenin.

To 243 mg 7-βgalactoxylcoumarin-3-carboxylic acid (U.S. Pat. No. 4,226,978) (0.66 mmol) and 84 mg N-hydroxysuccinimide (0.73 mmol) in 5 ml dimethylformamide under argon gas at 0° C. was added 143 mg dicyclohexylcarbodiimide (0.69 mmol). The mixture was allowed to warm from 0° C. to room temperature over 4 hours. To this mixture was added 322 mg 3-N-(6-aminohexyl)amino-3-desoxydigoxigenin (0.66 mmol), and the resulting solution allowed to stir overnight. The crude reaction mixture was adsorbed onto 1 g SilicAR® CC-7 (Mallinckrodt, St. Louis, Mo. USA) and applied to a 2.5×60 cm column of SilicAR® CC-7 packed with ethanol. The column was eluted with a linear gradient of 2 L ethanol to 2 L of a 4:1 ethanol-1M triethylammonium bicarbonate (pH 7.5) mixture. Fractions containing the product were pooled, evaporated, and the product was precipitated from methanol-1:1 ether/petroleum ether. Yield 124 mg. The sample was applied to a 2.5×60 cm column of Sephadex® LH-20 (Pharmacia) packed and eluted with methanol. The product was obtained by evaporation of solvent and precipitation from methanol-1:1 ether/hexane. Yield 72 mg (13%).

MP 152° C. (decomposed).

Analysis: Calculated for $C_{45}H_{62}N_2O_{13} \cdot 4H_2O$: C, 59.5; H, 7.8; N, 3.1. Found: C, 59.7; H, 7.0; N, 3.8.

¹NMR (90 mHz, DMSO-d₆): δ0.65 (s,3H); 0.86 (s,3H); 1.35 (m,26H); 2.3 (m,2H); 3,55 (m,13H); 4.06 (m,2H); 4,69 (m,3H); 4,87 (s,2H); 5.04 (d,J=7 Hz,1H); 5.82 (s,1H); 6.41 (m,1H); 7.15 (s,1H); 7.21 (d,J=8 Hz,1H); 7.93 (d,J=8 Hz,1H); 8.63 (bt,J=6 Hz,1H); 8.82 (s,1H).

IR(KCl): 1735, 1710, 1645, 1615, 1545, 1220, 1075 cm⁻¹.

Digoxigenin-FAD conjugate

To 25.2 mg 3-N-(5-carboxypentyl)amino-3-desoxdigoxigenin (50 μmol) and 6.3 mg N-hydroxysuccinimide (56 μmmol) in 0.5 ml dry dimethylformamide under argon gas at 0° C. was added a solution of 10.8 mg dicyclohexylcarbodiimide (52 μmol) in 0.6 ml dry dimethylsulfoxide. The reaction was stirred 30 minutes at 0° C. and 30 minutes at room temperature. A solution of 10 μmol N⁶-(6-aminohexyl)-flavin adenine dinucleotide (U.S. Pat. No. 4,255,566) in 1 ml H₁O was added to the above solution, and the mixture was allowed to stir overnight at room temperature. The reaction mixture was then diluted to 450 ml with H₂O and applied to a 1.5×30 centimeter (cm) column of DEAE-cellulose (bicarbonate form). The column was eluted with a linear gradient of 1.5 L H₂O to 1.5 L 0.1M triethylammonium bicarbonate (pH 7.5) at a flow rate of 2.8 ml/min. Fractions of 17 ml/min were taken. Fractions 16–32 contained the product and were pooled, concentrated, and adjusted to pH 7.0 and 25 ml volume. From the absorbance measurement at 450 nm (0.860) the yield was calculated as 1.903 μmol (19% yield) based on the millimolar extinction coefficient and FAD as 11.3.

EXAMPLE 4

Characterization of Digoxigenin-FAD

A sample (10 μl) of reaction mixture of the NOS ester of the digoxigenin carboxylic acid derivative and aminohexyl-FAD was chromatographed by thin layer chromatography using isobutyric acid-H₂O-triethylamine (70:29:1). The spot with $R_f=0.2$ was scraped from the plate and suspended in 1.0 ml 0.1M phosphate buffer, pH 7.0. A 0.35 ml aliquot of the supernatant was mixed with 100 μl of glucose oxidase assay reagent comprised of:
0.1M phosphate buffer, pH 7.0
2.1 mM sodium 3,5-dichloro-2-hydroxybenzene sulfonate
1.1% (w/v) bovine serum albumin
21 μg/ml peroxidase
0.105M glucose Apoglucose oxidase reagent was prepared consisting of 2 micromoler (μM) FAD binding sites; 10% (w/v) glycerol; 4 micromolar (mM) 4-aminoantipyrine, 0.1 molar (M) Phosphate, pH 7.0. Antiserum to digoxin (Atlantic Antibodies, Scarborough, Maine USA) was used diluted 10-fold with 0.1M phosphate, pH 7.0. A solution of digoxin (130 μM) in 0.1M phosphate, pH 7.0, was diluted 10-fold with the same buffer.

Assays were performed by placing 100 microliters (μl) of apoenzyme reagent and diluted digoxin antiserum in one corner of disposable cuvettes. Buffer or diluted digoxin solution (10 μl) was placed in the opposite corner. 1.90 ml of glucose oxidase assay reagent was added to start the reaction. The assays were incubated at 25° C. for 10 minutes and the absorbance at 520 nm recorded. The final concentration of digoxin was 65 nM.

| Antiserum to Digoxin (μl) | mA₅₂₀ₙₘ at 10 min.* | |
| --- | --- | --- |
| | Without Digoxin | With Digoxin |
| — | 797 | 740 |
| 5 | 463 | 716 |
| 10 | 391 | 505 |
| 20 | 354 | 378 |
| 30 | 344 | 339 |

*Average of duplicates corrected for blank activity in absence of label (mA₅₂₀ₙₘ = 105).

EXAMPLE 5

Titration of Antiserum to 3-N-(5-carboxypentyl)amino-3-desoxydigoxigenin

The titration was conducted with a substrate-labeled fluorescence immunoassay SLFIA; see U.S. Pat. No. 4,279,992) method using β-GU-digoxigenin conjugate, supra, as the labeled conjugate. Three milliliters of 50 nM Bicine buffer, pH 8.3, was measured into six cuvettes and the volumes of antiserum listed below were added to appropriate cuvettes. Then 100 μl of β-GU-digoxigenin with an absorbance at 340 nm of 0.01 was added. Finally, 100 μl of β-galactosidase from E. coli was added and the reactions were allowed to stand at ambient temperature for 20 minutes. (One unit of enzyme activity hydrolyzes 1 μmol of o-nitrophenyl-β-galactosidase per minute at 25° C. in 50 nM Bicine buffer, pH 8.3). At the end of this incubation period, the fluorescence was recorded using 400 nm light for excitation and 450 nm for emission. The following results were obtained:

| Antiserum (ml/assay) | Fluorescence (arbitrary units) |
| --- | --- |
| 0 | 94 |
| 1 | 80 |
| 2 | 66 |
| 5 | 32 |
| 10 | 35 |
| 20 | 32 |

The fluorescence decreased as the antiserum level increased; indicating that antibody was binding to the β-GU-digoxigenin conjugate.

EXAMPLE 6

Digoxin immunoassay

Various amounts of 2 μM digoxin were added to cuvettes containing 3.0 ml of 50 mM Bicine buffer, pH 8.3, to give the final digoxin concentrations listed below. One hundred microliters of β-galactosidase (0.6 unit/ml) in the Bicine buffer was added to each cuvette and the reactions were allowed to stand at ambient temperature for 20 minutes. At the end of this period, the fluorescence was recorded. The following results were obtained:

| Digoxin (mM) | Fluorescence (arbitrary units) |
| --- | --- |
| 0 | 39 |
| 7.6 | 44 |
| 15 | 52 |
| 38 | 65 |
| 152 | 85 |

As the digoxin level increased, the fluorescence increased, indicating that the digoxin and the β-GU-digoxigenin conjugate were competing for antibody binding sites.

What is claimed is:

1. A digoxigenin immunogen conjugate of the formula:

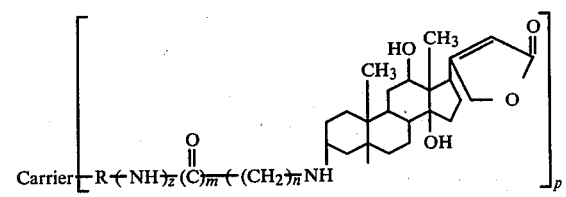

wherein Carrier is an immunogenic carrier material, R is a bond or a linking group, one of l and m is one and the other is zero, n is an integer from 2 through 10, and p is on the average from 1 to about 50.

2. The conjugate of claim 1 wherein R is a bond or a chain comprising between 1 and 20 atoms excluding hydrogen.

3. The conjugate of claim 1 wherein R is the residue of a bifunctional coupling agent linking the amino or carboxyl terminal group of the digoxigenin moiety to amino or carboxyl groups on the carrier material.

4. The conjugate of any one of claims 1–3 wherein said carrier material is an immunogenic protein or polypeptide.

5. A digoxigenin immunogen conjugate of the formula:

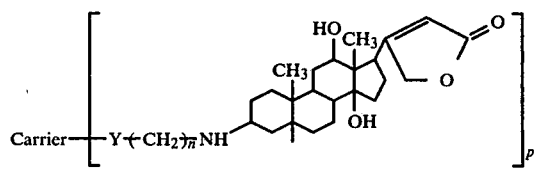

wherein Carrier is an immunogenic protein or polypeptide Carrier material, Y is an amide group linking carboxyl or amino groups on the carrier material to the digoxigenin moiety, n is an integer from 2 through 10, and p is on the average from 1 to the number of available amide coupling sites on the carrier material.

6. The conjugate of claim 5 wherein p is on the average between 1 and about 50.

7. The conjugate of claim 5 wherein said carrier material is an albumin.

8. The conjugate of claim 6 wherein the nitrogen atom in amide group Y is from an amino group in the carrier material and the carbon atom in amide group Y is bonded to the alkylene group in the formula.

9. The conjugate of claim 8 wherein $n=5$.

10. An antibody prepared against the conjugate of claim 1.

11. An antibody prepared against the conjugate of claim 5.

12. An antibody prepared against the conjugate of claim 9.

13. A digoxigenin derivative of the formula:

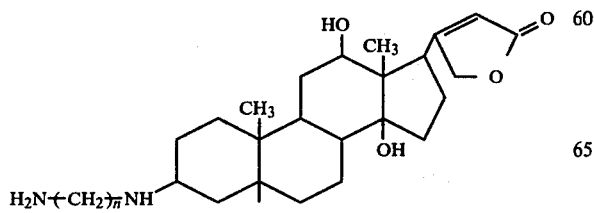

wherein n is an integer from 2 through 10.

14. The derivative of claim 13 wherein $n=6$.

15. In an immunoassay method for determining digoxin in a test sample, wherein the test sample is contacted with an antibody to digoxin and with a labeled conjugate comprising digoxin or a binding analog of digoxin and a label, and wherein thereafter the relative amount of the labeled conjugate that becomes bound to said antibody is determined, the improvement which comprises employing the antibody of claim 10, 11 or 12 as the antibody to digoxin.

16. A test kit for determining digoxin comprising a packaged unit comprising one or more containers holding (a) the antibody of claim 10, 11 or 12, and (b) a labeled digoxin or digoxigenin conjugate.

17. A test device for determining digoxin by homogeneous, immunoassay, comprising (a) a reagent composition including the antibody of claim 10, 11 or 12 and a labeled digoxin or digoxigenin conjugate which has a detectable property which is altered when bound by said antibody, and (b) a solid carrier member incorporated with said reagent composition.

18. A $\beta$-galactosyl-umbelliferone-digoxigenin conjugate of the formula:

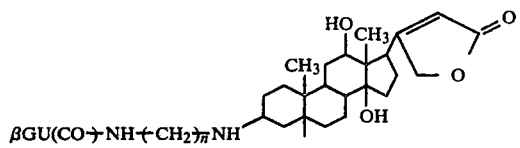

wherein $\beta GU(CO \rightarrow$ is

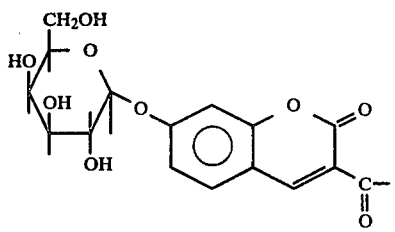

and n is an integer from 2 through 10.

19. The conjugate of claim 18 wherein $n=6$.

20. A flavin adenine dinucleotide-digoxigenin conjugate of the formula:

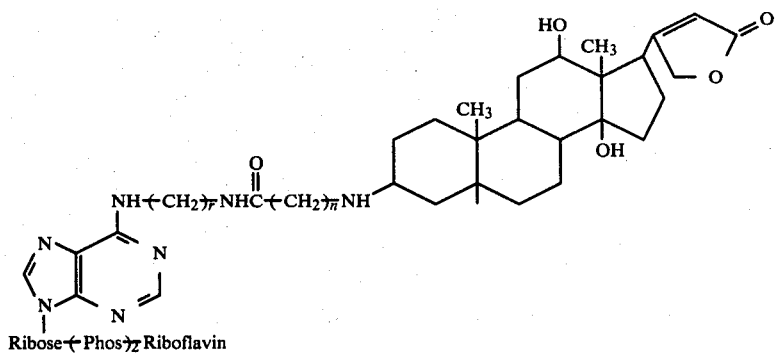
wherein Ribose-(Phos)$_2$-Riboflavin represents the riboflavin-pyrophosphate-ribose residue in flavin adenine dinucleotide, r is an integer from 2 through 10, and n is an integer from 2 through 10.
21. The conjugate of claim 20 wherein n=5.
22. The conjugate of claim 20 or 21 wherein r=6.

UNITED STATES PATENT AND TRADEMARK OFFICE
CERTIFICATE OF CORRECTION

PATENT NO. : 4,469,797
DATED      : September 4, 1984
INVENTOR(S): J. P. Albarella It is certified that error appears in the above-identified patent and that said Letters Patent are hereby corrected as shown below:

The structure in Claim 1 should be as follows:

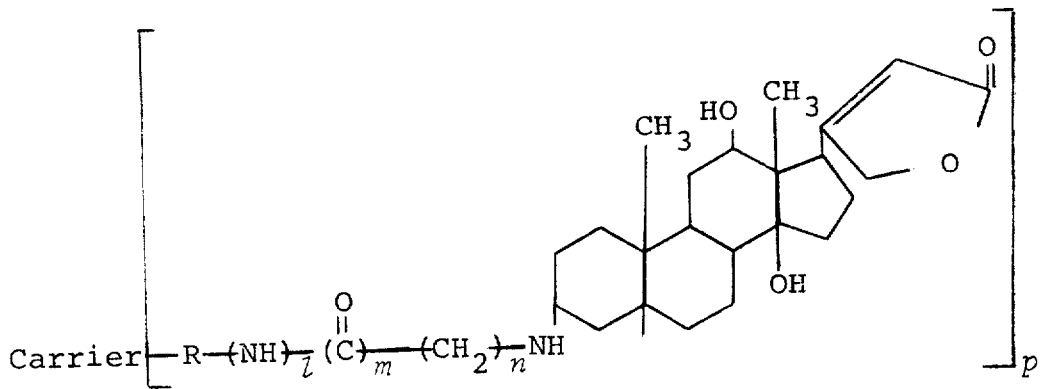

Signed and Sealed this

Twenty-sixth Day of February 1985

[SEAL]

Attest:

DONALD J. QUIGG

Attesting Officer   Acting Commissioner of Patents and Trademarks